United States Patent [19]

White et al.

[11] Patent Number: 5,522,852

[45] Date of Patent: Jun. 4, 1996

[54] SELECTIVE CARDIAC ACTIVITY ANALYSIS ATRIAL FIBRILLATION DETECTION SYSTEM AND METHOD AND ATRIAL DEFIBRILLATOR UTILIZING SAME

[75] Inventors: Harley White, Redmond; Joseph M. Bocek, Seattle, both of Wash.

[73] Assignee: InControl, Inc., Redmond, Wash.

[21] Appl. No.: 233,251

[22] Filed: Apr. 26, 1994

[51] Int. Cl.⁶ ..................................................... A61N 1/39
[52] U.S. Cl. ..................................................... 607/5
[58] Field of Search ............................... 607/4, 5, 9, 14; 128/702, 705

[56] References Cited

U.S. PATENT DOCUMENTS 5,391,185  2/1995  Kroll ............................................ 607/4

*Primary Examiner*—William E. Kamm
*Assistant Examiner*—Marianne Parker
*Attorney, Agent, or Firm*—Richard O. Gray, Jr.

[57] ABSTRACT

An atrial defibrillator applies cardioverting electrical energy to the atria of a human heart in need of cardioversion. The defibrillator includes an electrode pair and a sense amplifier associated with the atria of the heart for sensing electrical activity of the heart during a plurality of cardiac cycles to provide a cardiac signal. A detector is responsive to the cardiac signal for detecting cardiac events. During each cardiac cycle of the plurality of cardiac cycles, a time for counting is established wherein each time for counting has a total duration less than the duration of its corresponding cardiac cycle. A counter counts the cardiac events detected by the detector during the time for counting of the plurality of cardiac cycles to provide a cardiac event count. A comparator compares the cardiac event count to a predetermined cardiac event count. If the cardiac event count is greater than the predetermined cardiac event count, the atria are deemed to be in fibrillation and a cardiovertor applies cardioverting electrical energy to the atria to cardiovert the detected atrial fibrillation.

68 Claims, 1 Drawing Sheet

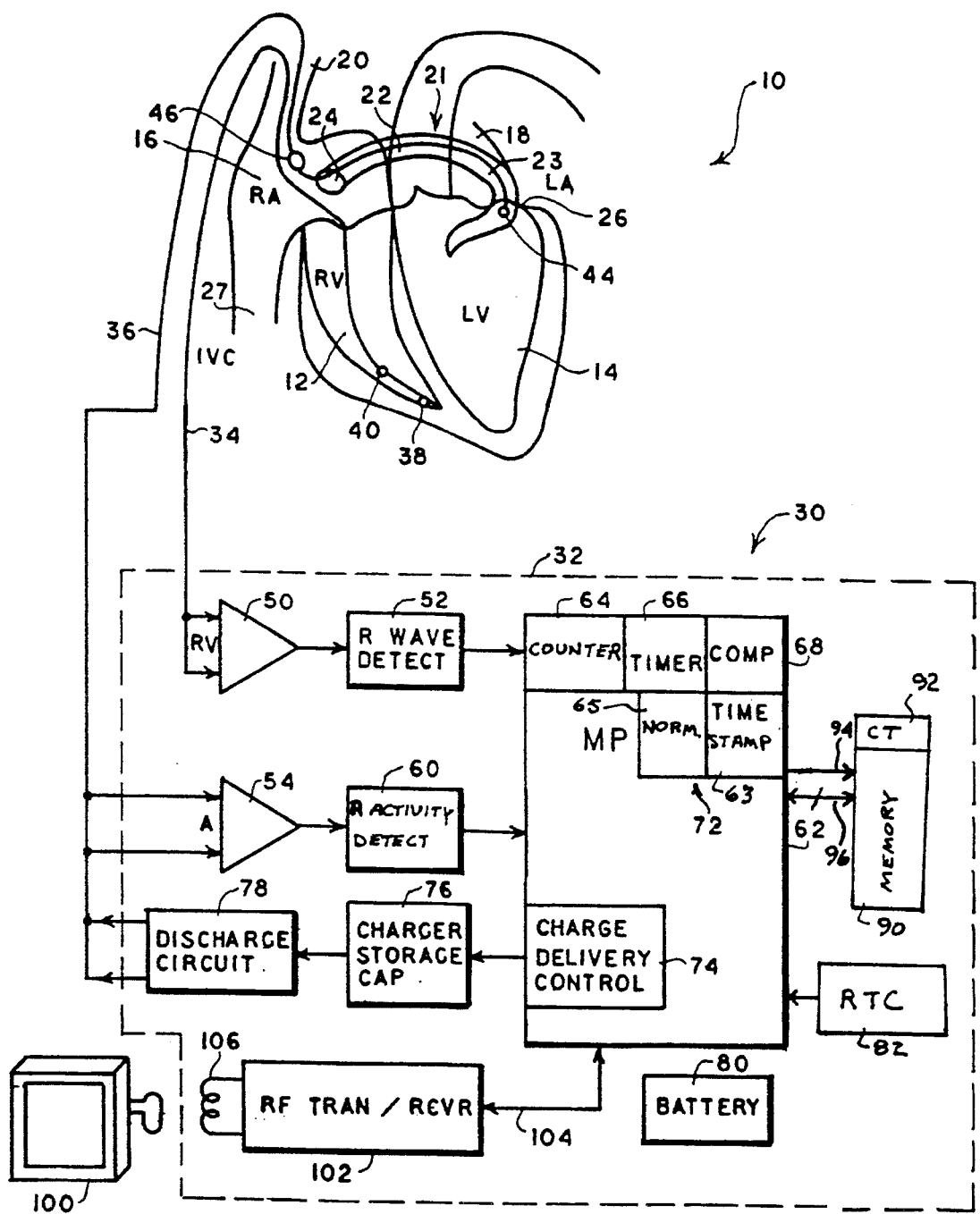

SELECTIVE CARDIAC ACTIVITY ANALYSIS ATRIAL FIBRILLATION DETECTION SYSTEM AND METHOD AND ATRIAL DEFIBRILLATOR UTILIZING SAME

BACKGROUND OF THE INVENTION

The present invention generally relates to an atrial defibrillator and method for applying cardioverting electrical energy to the atria of a human heart in need of cardioversion. The present invention is more particularly directed to an improved atrial fibrillation detection system and method for use in an implantable atrial defibrillator wherein cardiac activity detected in an atrial channel during selected portions of a plurality of cardiac cycles is analyzed for determining if the atria are in fibrillation. More specifically, the atrial fibrillation detection system and method of the present invention contemplates counting cardiac events detected in the atrial channel during the selected portions of the plurality of cardiac cycles and determining if the atria are in fibrillation responsive to the number of cardiac events counted.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, involves applying electrical defibrillating energy to the heart in synchronism with a detected ventricular electrical activation (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide patients suffering from occurrences of atrial fibrillation with relief. Unfortunately, to the detriment of such patients, none of these atrial defibrillators have become a commercial reality. Two such proposed defibrillators, although represented as being implantable, were not fully automatic, requiring human interaction for cardioverting or defibrillating the heart. Both of these proposed defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

In order for an implantable atrial defibrillator to be truly automatic, it must include an atrial fibrillation detector which, responsive to monitored activity of the heart, determines if the atria are in fibrillation. While numerous atrial fibrillation detection methods have been proposed in the past, they all generally contemplate the processing of rather complex algorithms. Such algorithms require extensive computational resources and generally take a significant amount of time to complete. The end result is that prior art atrial fibrillation detectors consume a significant amount of power. Since implantable atrial defibrillators are powered by a depletable power source, such as a battery, the predicted lifetime of an implantable atrial defibrillator can be greatly influenced by the amount of power consumed by its atrial fibrillation detector.

Hence, there is a need in the art for an improved atrial fibrillation detector which consumes little power during the detection of atrial fibrillation. Such an atrial fibrillation detector should require minimal computational resources and be able to complete its analysis in a short period of time. The present invention provides an atrial fibrillation detection system and method which consumes little power by requiring minimal computational resources and by being able to complete atrial fibrillation analysis in a short period of time.

SUMMARY OF THE INVENTION

The present invention therefore provides a system for detecting atrial fibrillation of a heart. The system includes sensing means associated with the atria of a heart for sensing electrical activity of the heart during a plurality of cardiac cycles of the heart and providing a cardiac signal, and means for establishing, for each cardiac cycle of the plurality of cardiac cycles, a time for analyzing. Each time for analyzing has a total duration less than the duration of its corresponding cardiac cycle. The system further includes analyzing means for analyzing the cardiac signal during the time for analyzing of the plurality of cardiac cycles, and determining means responsive to the analyzing means for determining if the atria of the heart are in fibrillation.

The present invention further provides an atrial defibrillator for applying cardioverting electrical energy to the atria of a human heart in need of cardioversion. The defibrillator includes sensing means associated with the atria of a heart for sensing electrical activity of the heart during a plurality of cardiac cycles of the heart and providing a cardiac signal and means for establishing, for each cardiac cycle of the plurality of cardiac cycles, a time for analyzing, wherein each time for analyzing has a total duration less than the duration of its corresponding cardiac cycle. The defibrillator further includes analyzing means for analyzing the cardiac signal during the time for analyzing of the plurality of cardiac cycles, determining means responsive to the analyzing means for determining if the atria of the heart are in fibrillation, and cardioverting means responsive to the determining means determining that the atria of the heart are in fibrillation for applying cardioverting electrical energy to the atria.

The present invention further provides a method for detecting atrial fibrillation of a heart. The method includes the steps of sensing electrical activity of the heart in or near at least one of the atria of the heart during a plurality of cardiac cycles of the heart to provide a cardiac signal and establishing, for each cardiac cycle of the plurality of cardiac cycles, a time for analyzing, wherein each time for analyzing has a total duration less than the duration of its corresponding cardiac cycle. The method further includes the steps of analyzing the cardiac signal during the time for analyzing of the plurality of cardiac cycles and determining if the atria of the heart are in fibrillation responsive to the analyzing of the cardiac signal.

The present invention still further provides a method of applying cardioverting electrical energy to the atria of a human heart in need of cardioversion. The method includes the steps of sensing electrical activity of the heart in or near at least one of the atria of the heart during a plurality of cardiac cycles of the heart to provide a cardiac signal and establishing, for each cardiac cycle of the plurality of cardiac cycles, a time for analyzing, wherein each time for analyzing has a total duration less than the duration of its corresponding cardiac cycle. The method further includes the steps of analyzing the cardiac signal during the time for analyzing of the plurality of cardiac cycles, determining if the atria of the heart are in fibrillation responsive to the analyzing of the cardiac signal, and applying cardioverting electrical energy to the atria of the heart if the atria of the heart are in fibrillation.

The present invention further provides a system for detecting atrial fibrillation of a heart. The system includes sensing means associated with the atria of a heart for sensing electrical activity of the heart during a plurality of cardiac cycles of the heart and providing a cardiac signal, detector means responsive to the cardiac signal for detecting cardiac events, and means for establishing, for each cardiac cycle of the plurality of cardiac cycles, a time for counting wherein each time for counting has a total duration less than the duration of its corresponding cardiac cycle. The system further includes counting means for counting the cardiac events detected by the detector means during the time for counting of the plurality of cardiac cycles to provide a cardiac event count and determining means for determining if the atria of the heart are in fibrillation responsive to the cardiac event count.

The present invention further provides an atrial defibrillator for applying cardioverting electrical energy to the atria of a human heart in need of cardioversion. The defibrillator includes sensing means associated with the atria of a heart for sensing electrical activity of the heart during a plurality of cardiac cycles of the heart and providing a cardiac signal, detector means responsive to the cardiac signal for detecting cardiac events, and means for establishing, for each cardiac cycle of the plurality of cardiac cycles, a time for counting, wherein each time for counting has a total duration less than the duration of its corresponding cardiac cycle. The defibrillator further includes counting means for counting the cardiac events detected by the detector means during the time for counting of the plurality of cardiac cycles to provide a cardiac event count, determining means for determining if the atria of the heart are in fibrillation responsive to the cardiac event count, and cardioverting means responsive to the determining means determining that the atria of the heart are in fibrillation for applying cardioverting electrical energy to the atria.

The present invention further provides a method for detecting atrial fibrillation of a heart. The method includes the steps of sensing electrical activity of the heart in or near at least one of the atria of the heart during a plurality of cardiac cycles of the heart to provide a cardiac signal, detecting cardiac events from the cardiac signal, and establishing, for each cardiac cycle of the plurality of cardiac cycles, a time for counting, wherein each time for counting has a total duration less than the duration of its corresponding cardiac cycle. The method further includes the steps of counting the cardiac events detected during the time for counting of the plurality of cardiac cycles to provide a cardiac event count and determining if the atria of the heart are in fibrillation responsive to the cardiac event count.

The present invention still further provides a method of applying cardioverting electrical energy to the atria of a human heart in need of cardioversion. The method includes the steps of sensing electrical activity of the heart in or near at least one of the atria of the heart during a plurality of cardiac cycles of the heart to provide a cardiac signal, detecting cardiac events from the cardiac signal, and establishing, for each cardiac cycle of the plurality of cardiac cycles, a time for counting, wherein each time for counting has a total duration less than the duration of its corresponding cardiac cycle. The method further includes the steps of counting the cardiac events detected during the time for counting of the plurality of cardiac cycles to provide a cardiac event count, determining if the atria of the heart are in fibrillation responsive to the cardiac event count, and applying cardioverting electrical energy to the atria of the heart if the atria of the heart are in need of cardioversion.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawing, in the sole FIGURE of which like reference numerals identify identical elements, and wherein the sole FIGURE is a schematic block diagram of a fully implantable atrial defibrillator embodying the present invention for applying defibrillating electrical energy to the atria of a human heart and which is shown in association with the human heart in need of atrial fibrillation monitoring and potential cardioversion of the atria.

DETAILED DESCRIPTION OF THE PREFERRED EMBODIMENT

Prior to referring to the sole FIGURE, a general description of a typical or normal cardiac cycle may be helpful in understanding the operation and various aspects of the present invention. The beginning of a cardiac cycle in normal sinus rhythm is initiated by a P wave which is normally a small positive wave. The P wave induces depolarization of the atria of the heart. Following the P wave there is a cardiac cycle portion which is substantially constant having a time duration on the order of, for example, 120 milliseconds.

The QRS complex of the cardiac cycle then normally occurs after the substantially constant portion. The dominating feature of the QRS complex is the R wave which is a rapid positive or negative deflection. The R wave generally has an amplitude greater than any other wave of the cardiac cycle and is characterized by a rapid deviation from and return toward baseline. The R wave is the depolarization of the ventricles and hence, as used herein, the term "ventricular activations" denotes R waves of the heart cardiac cycle. The QRS complex is completed by the S wave which is generally a small deflection which returns the cardiac cycle to baseline.

Following the S wave of the QRS complex, the T wave occurs which is separated from the QRS complex by about 250 milliseconds. The T wave is relatively long in duration of, for example, on the order of 150 milliseconds. The cardiac cycle segment between the S wave and the T wave is commonly referred to as the ST segment.

The next cardiac cycle begins with the next P wave. The duration of a cardiac cycle may be on the order of 800 milliseconds. While the P wave in actuality initiates each new cardiac cycle, cardiac cycles are generally timed based upon detected R to R intervals because R wave detection is generally thought to be most reliable given the extreme amplitude and spiked shape of the R waves. Hence, as used herein, the term "cardiac cycle" is meant to denote the activity of the heart during immediately succeeding R waves.

As will be appreciated by those skilled in the art, the characteristics of the cardiac cycles of a heart experiencing atrial fibrillation are distinctly different than that described for normal sinus rhythm. During normal sinus rhythm, there are discernible P waves and portions of the cardiac cycle, as for example during the ST segment, when there is little if any atrial activity. In contrast, during atrial fibrillation, there are no discernable P waves and because the atria are in an unstable or fibrillating condition, there is detectable atrial activity even during those portions of a cardiac cycle, such as the ST segment, when there is little or no atrial activity during normal sinus rhythm. The present invention, as will be seen hereinafter, utilizes this difference between the characteristics of the cardiac cycles during atrial fibrillation and the characteristics of the cardiac cycles during normal sinus rhythm to advantage for detecting the presence of atrial fibrillation.

Referring now to the sole FIGURE, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in the sole FIGURE are the right ventricle 12, the left ventricle 14, the right atrium 16, and left atrium 18, the superior vena cava 20, the coronary sinus channel 21 which, as used herein, denotes the coronary sinus 22 and the great cardiac vein 23, the coronary sinus ostium or opening 24, the left ventricular free wall 26 and the inferior vena cava 27.

The atrial defibrillator 30 generally includes an enclosure 32 for hermetically sealing the internal circuit elements of the atrial defibrillator to be described hereinafter, an intravascular first lead 36, and an endocardial second lead 34. The enclosure 32 and first and second leads 36 and 34 are arranged to be implanted beneath the skin of a patient so as to render the atrial defibrillator 30 fully implantable.

The first lead 36 generally includes a first or tip electrode 44 and a second or proximal electrode 46. As illustrated, the second lead 36 is flexible and arranged to be passed down the superior vena cava 20, into the right atrium, into the coronary sinus ostium 24, and advanced into the coronary sinus channel 21 of the heart near the left side thereof so that the first or tip electrode 44 is within the coronary sinus channel 21 either within the coronary sinus 22 adjacent the left ventricle 14 and beneath the left atrium 18 or most preferably within the great cardiac vein 23 adjacent the left ventricle 14 and beneath the left atrium 18. The electrodes 44 and 46 are spaced apart such that when the first electrode 44 is positioned as described above, the second electrode 46 is in the right atrium 16. The first electrode 44 together with the second electrode 46 provide bi-polar sensing of heart activity in the atria 16 and 18.

The first electrode 44 and the second electrode 46 further provide for the delivery of defibrillating electrical energy to the atria. Because the first electrode 44 is located beneath the left atrium 18 near the left ventricle 14 and the second electrode 46 is within the right atrium 16, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized. This greatly reduces the potential for ventricular fibrillation of the heart to be induced as a result of the application of defibrillating electrical energy to the atria of the heart.

The second lead 34 preferably comprises an endocardial bi-polar lead having electrodes 38 and 40 arranged for establishing electrical contact with the right ventricle 12 of the heart 10. The electrodes 38 and 40 permit bi-polar sensing of ventricular activations in the right ventricle. As illustrated, the lead 34 is fed through the superior vena cava 20, into the right atrium 16, and then into the right ventricle 12.

Within the enclosure 32, the atrial defibrillator 30 includes a first sense amplifier 54, an atrial activity detector 60, a second sense amplifier 50, and an R wave detector 52. The first sense amplifier 54 forms a first sensing means which together with electrodes 44 and 46 of the first lead 36 to which sense amplifier 54 is coupled, senses cardiac activity of the heart in or near the atria 16 and 18 and provides a cardiac signal to the atrial activity detector 60. The sense amplifier 50 forms a second sensing means which, together with electrodes 38 and 40 of the second lead 34 to which it is coupled senses cardiac activity in the right ventricle of the heart to provide a second cardiac signal to the R wave detector 52. Preferably both the sense amplifier 54 and the sense amplifier 50 include a differentiating filter so that the first cardiac signal provided by sense amplifier 54 and the second cardiac signal provided by sense amplifier 50 are differentiated first and second cardiac signals respectively.

The R wave detector 52 provides one or more output pulses for each R wave sensed during a cardiac cycle of the heart. To that end, the R wave detector may include a further differentiating filter for differentiating the differentiated second cardiac signal provided by sense amplifier 50 resulting in a twice differentiated second cardiac signal. The R wave detector 52 may further include a threshold circuit for setting an upper and lower threshold which provides an output when the twice differentiated second cardiac signal transitions beyond either the upper or lower thresholds.

Finally, the R wave detector preferably further includes an output pulse rate limiter having a programmable pulse repetition time interval. The pulse repetition time interval limits the number of output pulses issued for each detected R wave. It also allows one such pulse to indicate the completion of each detected R wave so that the end of each R wave may be determined. As an example, the repetition time interval may be eight milliseconds.

The atrial activity detector 60 preferably also includes a differentiating filter for differentiating the differentiated first cardiac signal provided by sense amplifier 54 to provide a twice differentiated first cardiac signal and a threshold circuit for setting an upper and lower threshold to provide an output when the twice differentiated first cardiac signal transitions beyond either the upper or lower threshold. The atrial activity detector 60 also preferably includes an output pulse rate limiter. The repetition time interval of this limiter is also preferably programmable and set to, for example, eight milliseconds.

The enclosure 32 of the atrial defibrillator 30 further includes a microprocessor 62. The microprocessor 62 is preferably implemented in accordance with this embodiment of the present invention to result in a plurality of functional stages. The stages include a time stamp stage 63, a counter stage 64, a normalizing stage 65, a timer stage 66, and a comparator stage 68, all of which form an atrial fibrillation detector 72 embodying the present invention, and a charge delivery and energy control stage 74.

The microprocessor 62 is arranged to operate in conjunction with a memory 90 which is coupled to the microprocessor 62 by a multiple-bit address bus 94 and a bi-directional multiple-bit data bus 96. This permits the microprocessor 62 to address desired memory locations within the memory for executing write or read operations. During a write operation, the microprocessor stores data, such as time stamps, or operating parameters, such as the times for counting to be referred to hereinafter, in the memory at the addresses defined by multiple-bit addresses conveyed over the address bus 94 and conveys the operating parameters and data to the memory 90 over the multiple-bit data bus 96. During a read operation, the microprocessor 62 obtains data or operating parameters from the memory at the storage locations identified by the multiple-bit addresses provided over the address bus 94 and receives the operating parameters and data from the memory over the bi-directional data bus 96.

For entering operating parameters into the memory 90, as for example the times for counting into memory portion 92, the microprocessor 62 receives the programmable operating parameters from an external controller 100 which is external to the skin of the patient. The external controller 100 is arranged to communicate with a receiver/transmitter 102 within enclosure 32 which is coupled to the microprocessor 62 over a bi-directional bus 104. The receiver/transmitter 102 conveys various information which it obtains from the microprocessor 62 to the external controller 100 or for receiving programming parameters from the external controller 100 which the receiver/transmitter 102 then conveys to the microprocessor 62 for storage in memory 90.

The receiver/transmitter 102 includes a transmitting coil 106 so that the receiver/transmitter 102 and coil 106 form a communication means. Such communication means are well known in the art and may be utilized as noted above for receiving commands from external to the implantable enclosure 32 and for transmitting data to the external controller 100 from the implanted enclosure 32. One preferred communication system is disclosed in copending U.S. application Ser. No. 08/001,330, filed Jan. 7, 1993 for "Telemetry System for an Implantable Cardiac Device", which application is assigned to the assignee of the present invention and incorporated herein by reference.

To complete the identification of the various structural elements within the enclosure 32, the atrial defibrillator 30 further includes a charger and storage capacitor circuit 76 of the type well known in the art which charges a storage capacitor to a selected peak voltage and a discharge circuit 78 for discharging the storage capacitor within circuit 76 for a predetermined time to provide a controlled discharge output of electrical energy when required to the atria of the heart. To that end, the discharge circuit 78 is coupled to the first electrode 44 and the second electrode 46 of lead 36 for applying the cardioverting or defibrillating electrical energy to the atria. Lastly, the defibrillator 30 includes a depletable power source 80, such as a lithium battery, for providing power to the electrical components of the atrial defibrillator 30, and a real time clock 82.

At spaced apart times, the real time clock 82 enables the microprocessor 62 which in turn enables the sense amplifiers 50 and 54, the R wave detector 52, and the atrial activity detector 60 to initiate a heart activity sensing time, herein referred to as a data acquisition period. The data acquisition period is timed by the timer 66 and preferably has a duration of, for example, eight seconds. During the eight second data acquisition period, each output or burst of closely spaced outputs of the R wave detector 52, denoting the detection of an R wave, and each output of the atrial activity detector 60, denoting the detection of a cardiac event sensed by the electrodes 44 and 46 and sense amplifier 54, causes an interrupt to the microprocessor 62. Each interrupt is classified as either being a detected R wave or a detected cardiac event and time stamped by the time stamp stage 63. Each time stamp is then stored in the memory 90 according to its classification. After the eight second data acquisition period is completed, the atrial fibrillation detector 72 determines if the atria 16 and 18 are in fibrillation in a manner to be described hereinafter and in accordance with this preferred embodiment of the present invention. If the atria are in fibrillation and thus in need of cardioversion, the charge delivery control 74 causes the charger and storage capacitor circuit 76 to charge the storage capacitor within the circuit 76 to a selected peak voltage. Thereafter, and in timed relation to a detected R wave, the atrial defibrillator 30, through the discharge circuit 78, applies a portion of the stored electrical energy to electrodes 44 and 46 and thus the atria 16 and 18 to cardiovert the atria 16 and 18.

In accordance with this preferred embodiment of the present invention, the atrial fibrillation detector 72 determines if the atria are in fibrillation in response to the number of cardiac events detected by the atrial activity detector 60 during predetermined times for counting of the data acquisition period. More specifically, a predetermined time for counting is established for each cardiac cycle occurring during the eight second acquisition period. Each time for counting has a total duration less than the duration of its corresponding cardiac cycle. In accordance with this preferred embodiment, each time for counting consists of a single counting period for each cardiac cycle occurring during the data acquisition period and is selected to correspond to a portion of each cardiac cycle wherein, during normal sinus rhythm, there should be little if any atrial activity of the heart. For example, and as is still further contemplated in accordance with this preferred embodiment, each time for counting, for each cardiac cycle occurring during the data acquisition period, is selected to begin about 60 milliseconds after the last output pulse of R wave detector 52 for each R wave detected (denoting the completion of each R wave) and to terminate about 140 milliseconds thereafter or about 200 milliseconds after the detection of each such R wave. By timing the time for counting off of the last output pulse of R wave detector 52 for each R wave, it will be assured that the time for counting begins after the R wave has been completed. This time for counting, as will be appreciated from the description of a normal cardiac cycle, will correspond to a portion of the ST segment of each cardiac cycle, beginning after the R wave and terminating before the T wave of each cardiac cycle.

As previously mentioned, the time for counting is stored in the memory portion 92 of memory 90. After the eight second data acquisition period is completed, the microprocessor 62 accesses the time stamps stored in the memory 90. It determines when each cardiac cycle began from the R wave time stamps stored in the memory and based thereon establishes the time for counting for each cardiac cycle to determine which time stamps are to be counted. Taking each cardiac cycle one at a time, the counter 64 counts the cardiac event time stamps generated responsive to the atrial activity detector 60 that occurred during the counting period of each cardiac cycle. The counter maintains a cumulative count over the data acquisition period. When the time stamps to be counted for each cardiac cycle have been counted, the counter thus provides a cumulative cardiac event count.

The comparator stage 68, responsive to the cardiac event count, determines if the atria are in fibrillation. In doing so, the comparator 68 performs a comparison against a predetermined event count. The comparison may be implemented in accordance with a number of different methods. Four such methods are described herein.

First, the comparison may be based upon the total cardiac event count. If the total cardiac event count is greater than a predetermined event count, for example a predetermined event count of 24 counts, atrial fibrillation will be considered to be present and the charge and delivery control 74 will cause the storage capacitor of circuit 76 to begin charging.

Second, the comparison may be based upon an average cardiac cycle event count. To implement this comparison, the normalizing stage 65 divides the total cardiac event count by the number of cardiac cycles occurring during the eight second data acquisition period to determine an average cardiac cycle event count. The comparator 68 then determines if the average cardiac cycle event count is greater than a predetermined average cardiac cycle event count. If it is, atrial fibrillation will be considered to be present and the charge and delivery control 74 will cause the storage capacitor of circuit 76 to begin charging.

Third, the comparison may be based upon an average event count per unit of time, for example per second of the data acquisition period. To implement this method, the normalizing stage 65 divides the total cardiac event count by the duration (in seconds) of the acquisition period, as for example, by eight seconds in accordance with this preferred embodiment. The normalizing stage 65 hence determines an average event count per second which is then compared to a predetermined average event count per second by the comparator 68. If the determined average event count per second is greater than a predetermined average event count per second, for example three event counts per second, atrial fibrillation will be considered to be present and the charge and delivery control 74 will cause the storage capacitor of circuit 76 to begin charging.

Fourth, and preferably, the comparison may be based upon an average event count per unit of counting time. To implement this method, the total event count may be divided by the actual total counting time, in seconds. If the average event count per unit of counting time is greater than a predetermined average, atrial fibrillation will be considered to be present.

Hence, as can be seen from the foregoing, a time for analyzing the cardiac signal is provided for each cardiac cycle of the acquisition period. The cardiac signal is analyzed by the atrial activity detector 60 by detecting cardiac events and by the counter 64 counting the number of cardiac events occurring during the analysis periods (counting periods). Because the time for counting the cardiac events is chosen to correspond to a portion of the cardiac cycles wherein, during normal sinus rhythm, little if any atrial activity is expected, the atrial fibrillation detector of the present invention is extremely specific in detecting atrial fibrillation. Such specificity is made possible even though the electrodes 44 and 46 are spaced apart by a distance which is greater than the distance in which a localized bi-polar sensing electrode pair would be spaced. In addition, the determination of the presence or absence of atrial fibrillation, by virtue of the present invention, is accomplished with minimal computational resources and in a short period of time which conserves battery power in achieving that end.

While a particular embodiment of the present invention has been shown and described, modifications may be made. For example, instead of counting cardiac events based upon prestored time stamps, the cardiac events may be counted in real time by the microprocessor as they occur during the time for counting of each cardiac cycle. Further, and as will be appreciated by those skilled in the art, the broader aspects of the present invention are not intended to be limited to the particular atrial fibrillation detection method disclosed herein. Other numerical analysis methods for detecting atrial fibrillation may be employed to advantage while practicing the broader aspects of the present invention of establishing the analysis periods as disclosed herein. Hence, it is intended in the appended claims, to cover all such changes and modifications which may fall within the true spirit and scope of the invention.

What is claimed is:

1. A system for detecting atrial fibrillation of a heart, said system comprising:

sensing means for sensing electrical activity of the heart during a plurality of cardiac cycles of the heart and providing a cardiac signal;

means for establishing, for each said cardiac cycle of said plurality of cardiac cycles, a time for analyzing, each said cardiac cycle having a duration and each said time for analyzing having a total duration less than the duration of its corresponding cardiac cycle;

analyzing means for analyzing said cardiac signal during the time for analyzing of said plurality of cardiac cycles; and determining means responsive to said analyzing means for determining if the atria of the heart are in fibrillation.

2. A system as defined in claim 1 wherein each said time for analyzing consists of a single analysis period for each said cardiac cycle.

3. A system as defined in claim 1 further including second sensing means for sensing ventricular electrical activity of the heart, and detector means responsive to said second sensing means for detecting R waves of the heart, and wherein said means for establishing is responsive to said detected R waves for establishing each respective said time for analyzing.

4. A system as defined in claim 3 wherein each said time for analyzing consists of a single analysis period for each said cardiac cycle of said plurality of cardiac cycles.

5. A system as defined in claim 4 wherein said means for establishing begins each said analysis period after the completion of each said detected R wave of each said cardiac cycle and terminates each said analysis period before the T wave of each said cardiac cycle.

6. A system as defined in claim 5 wherein said means for establishing begins each said analysis period about sixty milliseconds after the detected completion of each said detected R wave of each said cardiac cycle and terminates each said analysis period about two hundred milliseconds after the detected completion of each said detected R wave of each said cardiac cycle.

7. An atrial defibrillator for applying cardioverting electrical energy to the atria of a human heart in need of cardioversion, said defibrillator comprising:

sensing means for sensing atrial electrical activity of the heart during a plurality of cardiac cycles of the heart and providing a cardiac signal;

means for establishing, for each said cardiac cycle of said plurality of cardiac cycles, a time for analyzing, each said cardiac cycle having a duration and each said time for analyzing having a total duration less than the duration of its corresponding cardiac cycle;

analyzing means for analyzing said cardiac signal during the time for analyzing of said plurality of cardiac cycles;

determining means responsive to said analyzing means for determining if the atria of the heart are in fibrillation; and cardioverting means responsive to said determining means determining that the atria of the heart are in fibrillation for applying cardioverting electrical energy to the atria.

8. A defibrillator as defined in claim 7 wherein each said time for analyzing consists of a single analysis period for each said cardiac cycle.

9. A defibrillator as defined in claim 7 further including second sensing means for sensing ventricular electrical activity of the heart, and detector means responsive to said second sensing means for detecting R waves of the heart, and wherein said means for establishing is responsive to said detected R waves for establishing each respective said time for analyzing.

10. A defibrillator as defined in claim 9 wherein each said time for analyzing consists of a single analysis period for each said cardiac cycle of said plurality of cardiac cycles.

11. A defibrillator as defined in claim 10 wherein said means for establishing begins each said analysis period after the completion of each said detected R wave of each said cardiac cycle and terminates each said analysis period before the T wave of each said cardiac cycle.

12. A defibrillator as defined in claim 11 wherein said means for establishing begins each said analysis period about sixty milliseconds after the detected completion of each said detected R wave of each said cardiac cycle and terminates each said analysis period about two hundred milliseconds after the detected completion of each said detected R wave of each said cardiac cycle.

13. A method for detecting atrial fibrillation of a heart, said method including the steps of:

sensing electrical activity of the heart in or near at least one of the atria of the heart during a plurality of cardiac cycles of the heart to provide a cardiac signal;

establishing, for each said cardiac cycle of said plurality of cardiac cycles, a time for analyzing, each said cardiac cycle having a duration and each said time for analyzing having a total duration less than the duration of its corresponding cardiac cycle;

analyzing the cardiac signal during the time for analyzing of said plurality of cardiac cycles; and determining if the atria of the heart are in fibrillation responsive to the analyzing of said cardiac signal.

14. A method as defined in claim 13 wherein said establishing step includes establishing a single analysis period for each said cardiac cycle.

15. A method as defined in claim 13 including the further step of detecting R waves of the heart, and wherein said establishing step includes establishing each respective said time for analyzing with respect to a detected R wave.

16. A method as defined in claim 15 wherein said establishing step includes establishing a single analysis period for each said cardiac cycle of said plurality of cardiac cycles.

17. A method as defined in claim 16 wherein said establishing step includes beginning each said analysis period after the completion of each said detected R wave of each said cardiac cycle and terminating each said analysis period before the T wave of each said cardiac cycle.

18. A method as defined in claim 17 wherein said establishing step includes beginning each said analysis period about sixty milliseconds after the detected completion of each said detected R wave of each said cardiac cycle and terminating each said analysis period about two hundred milliseconds after the detected completion of each said detected R wave of each said cardiac cycle.

19. A method of applying cardioverting electrical energy to the atria of a human heart in need of cardioversion, said method including the steps of:

sensing electrical activity of the heart in or near at least one of the atria of the heart during a plurality of cardiac cycles of the heart to provide a cardiac signal;

establishing, for each said cardiac cycle of said plurality of cardiac cycles, a time for analyzing, each said cardiac cycle having a duration and each said time for analyzing having a total duration less than the duration of its corresponding cardiac cycle;

analyzing the cardiac signal during the time for analyzing of said plurality of cardiac cycles;

determining if the atria of the heart are in fibrillation responsive to the analyzing of said cardiac signal; and applying cardioverting electrical energy to the atria of the heart if the atria of the heart are in fibrillation.

20. A method as defined in claim 19 wherein said establishing step includes establishing a single analysis period for each said cardiac cycle.

21. A method as defined in claim 19 including the further steps of detecting R waves of the heart, and wherein said establishing step includes establishing each respective said time for analyzing with respect to a detected R wave.

22. A method as defined in claim 21 wherein said establishing step includes establishing a single analysis period for each said cardiac cycle of said plurality of cardiac cycles.

23. A method as defined in claim 22 wherein said establishing step includes beginning each said analysis period after the completion of each said detected R wave of each said cardiac cycle and terminating each said analysis period before the T wave of each said cardiac cycle.

24. A method as defined in claim 23 wherein said establishing step includes beginning each said analyzing period about sixty milliseconds after the detected completion of each said detected R wave of each said cardiac cycle and terminating each said analyzing period about two hundred milliseconds after the detected completion of each said detected R wave of each said cardiac cycle.

25. A system for detecting atrial fibrillation of a heart, said system comprising:

sensing means for sensing atrial electrical activity of the heart during a plurality of cardiac cycles of the heart and providing a cardiac signal;

detector means responsive to said cardiac signal for detecting cardiac events;

means for establishing, for each said cardiac cycle of said plurality of cardiac cycles, a time for counting, each said cardiac cycle having a duration and each said time for counting having a total duration less than the duration of its corresponding cardiac cycle;

counting means for counting the cardiac events detected by said detector means during the time for counting of said plurality of cardiac cycles to provide a cardiac event count; and determining means for determining if the atria of the heart are in fibrillation responsive to said cardiac event count.

26. A system as defined in claim 25 wherein said determining means includes means for determining if said cardiac event count is greater than a predetermined event count.

27. A system as defined in claim 25 further including normalizing means for determining an average cardiac cycle event count for said plurality of cardiac cycles and wherein said determining means includes means for determining if said average cardiac cycle event count is greater than a predetermined average cardiac cycle event count.

28. A system as defined in claim 25 further including a timer for establishing a heart activity sensing time, wherein said sensing means senses said electrical activity of the heart during said heart activity sensing time, wherein said system further includes normalizing means for determining an average event count per unit of time for said plurality of cardiac cycles, and wherein said determining means includes means for determining if said average event count per unit of time is greater than a predetermined average event count per unit of time.

29. A system as defined in claim 25 further including normalizing means for determining an average event count per unit of time of a total counting time, and wherein said determining means includes means for determining if said average event count per unit of total counting time is greater than a predetermined average event count per unit of total counting time.

30. A system as defined in claim 25 wherein each said time for counting consists of a single counting period for each said cardiac cycle.

31. A system as defined in claim 25 further including second sensing means associated with at least one ventricle of the heart for sensing ventricular electrical activity of the heart, and second detector means responsive to said second sensing means for detecting R waves of the heart, and wherein said means for establishing is responsive to said detected R waves for establishing each respective said time for counting.

32. A system as defined in claim 31 wherein each said time for counting consists of a single counting period for each said cardiac cycle of said plurality of cardiac cycles.

33. A system as defined in claim 32 wherein said means for establishing begins each said counting period after the completion of each said detected R wave of each said cardiac cycle and terminates each said counting period before the T wave of each said cardiac cycle.

34. A system as defined in claim 33 wherein said means for establishing begins each said counting period about sixty milliseconds after the detected completion of each said detected R wave of each said cardiac cycle and terminates each said counting period about two hundred milliseconds after the detected completion of each said detected R wave of each said cardiac cycle.

35. A system as defined in claim 25 further including time stamp means for generating a time stamp for each one of said detected cardiac events, memory means for storing said time stamps, and wherein said counting means counts only said time stamps stored in said memory means occurring during each said time for counting.

36. An atrial defibrillator for applying cardioverting electrical energy to the artria of a human heart in need of cardioversion, said defibrillator comprising:

sensing means for sensing atrial electrical activity of the heart during a plurality of cardiac cycles of the heart and providing a cardiac signal;

detector means responsive to said cardiac signal for detecting cardiac events;

means for establishing, for each said cardiac cycle of said plurality of cardiac cycles, a time for counting, each said cardiac cycle having a duration and each said time for counting having a total duration less than the duration of its corresponding cardiac cycle;

counting means for counting the cardiac events detected by said detector means during the time for counting of said plurality of cardiac cycles to provide a cardiac event count;

determining means for determining if the atria of the heart are in fibrillation responsive to said cardiac event count; and cardioverting means responsive to said determining means determining that the atria of the heart are in fibrillation for applying cardioverting electrical energy to the atria.

37. A defibrillator as defined in claim 36 wherein said determining means includes means for determining if said cardiac event count is greater than a predetermined event count.

38. A defibrillator as defined in claim 36 further including normalizing means for determining an average cardiac cycle event count for said plurality of cardiac cycles and wherein said determining means includes means for determining if said average cardiac cycle event count is greater than a predetermined average cardiac cycle event count.

39. A defibrillator as defined in claim 36 further including a timer for establishing a heart activity sensing time, wherein said sensing means senses said electrical activity of the heart during said heart activity sensing time, wherein said system further includes normalizing means for determining an average event count per unit of time for said plurality of cardiac cycles, and wherein said determining means includes means for determining if said average event count per unit of time is greater than a predetermined average event count per unit of time.

40. A defibrillator as defined in claim 36 further including a normalizing means for determining an average event count per unit of time of a total counting time, and wherein said determining means includes means for determining if said average event count per unit of total counting time is greater than a predetermined average event count per unit of total counting time.

41. A defibrillator as defined in claim 36 wherein each said time for counting consists of a single counting period for each said cardiac cycle.

42. A defibrillator as defined in claim 36 further including second sensing means for sensing ventricular electrical activity of the heart, and second detector means responsive to said second sensing means for detecting R waves of the heart, and wherein said means for establishing is responsive to said detected R waves for establishing each respective said time for counting.

43. A defibrillator as defined in claim 42 wherein each said time for counting consists of a single counting period for each said cardiac cycle of said plurality of cardiac cycles.

44. A defibrillator as defined in claim 43 wherein said means for establishing begins each said counting period after the completion of each said detected R wave of each said cardiac cycle and terminates each said counting period before the T wave of each said cardiac cycle.

45. A defibrillator as defined in claim 44 wherein said means for establishing begins each said counting period about sixty milliseconds after the detected completion of each said detected R wave of each said cardiac cycle and terminates each said counting period about two hundred milliseconds after the detected completion of each said detected R wave of each said cardiac cycle.

46. A defibrillator as defined in claim 36 further including time stamp means for generating a time stamp for each one of said detected cardiac events, memory means for storing said time stamps, and wherein said counting means counts only said time stamps stored in said memory means occurring during each said time for counting.

47. A method for detecting atrial fibrillation of a heart, said method including the steps of:

sensing electrical activity of the heart in or near at least one of the atria of the heart during a plurality of cardiac cycles of the heart to provide a cardiac signal;

detecting cardiac events from said cardiac signal;

establishing, for each said cardiac cycle of said plurality of cardiac cycles, a time for counting, each said cardiac cycle having a duration and each said time for counting having a total duration less than the duration of its corresponding cardiac cycle;

counting the cardiac events detected during the time for counting of said plurality of cardiac cycles to provide a cardiac event count; and determining if the atria of the heart are in fibrillation responsive to said cardiac event count.

48. A method as defined in claim 47 wherein said determining step includes determining if said cardiac event count is greater than a predetermined event count.

49. A method as defined in claim 47 including the further step of providing an average cardiac cycle event count for said plurality of cardiac cycles and wherein said determining step includes determining if said average cardiac cycle event count is greater than a predetermined average cardiac cycle event count.

50. A method as defined in claim 47 including the further step of establishing a heart activity sensing time, wherein said sensing step includes sensing said atrial electrical activity of the heart during said heart activity sensing time, wherein said method further includes the step of providing an average event count per unit of time for said plurality of cardiac cycles, and wherein said determining step includes determining if said average event count per unit of time is greater than a predetermined average event count per unit of time.

51. A method as defined in claim 47 including the further step of determining a total counting time for said plurality of cardiac cycles, wherein said method further includes the step of providing an average event count per unit of total counting time for said plurality of cardiac cycles, and wherein said determining step includes determining if said average event count per unit of total counting time is greater than a predetermined average event count per unit of counting time.

52. A method as defined in claim 47 wherein said establishing step includes establishing a single counting period for each said cardiac cycle.

53. A method as defined in claim 47 including the further step of detecting R waves of the heart, and wherein said establishing step includes establishing each respective said time for counting with respect to a detected R wave.

54. A method as defined in claim 53 wherein said establishing step includes establishing a single counting period for each said cardiac cycle of said plurality of cardiac cycles.

55. A method as defined in claim 54 wherein said establishing step includes beginning each said counting period after the completion of each said detected R wave of each said cardiac cycle and terminating each said counting period before the T wave of each said cardiac cycle.

56. A method as defined in claim 55 wherein said establishing step includes beginning each said counting period about sixty milliseconds after the detected completion of each said detected R wave of each said cardiac cycle and terminating each said counting period about two hundred milliseconds after the detected completion of each said detected R wave of each said cardiac cycle.

57. A method as defined in claim 47 including the further steps of generating a time stamp for each one of said detected cardiac events, providing a memory, and storing said time stamps in said memory, and wherein said counting step includes counting only said time stamps stored in said memory occurring during each said time for counting.

58. A method of applying cardioverting electrical energy to the atria of a human heart in need of cardioversion, said method including the steps of:

sensing electrical activity of the heart in or near at least one of the atria of the heart during a plurality of cardiac cycles of the heart to provide a cardiac signal;

detecting cardiac events from said cardiac signal;

establishing, for each said cardiac cycle of said plurality of cardiac cycles, a time for counting, each said cardiac cycle having a duration and each said time for counting having a total duration less than the duration of its corresponding cardiac cycle;

counting the cardiac events detected during the time for counting of said plurality of cardiac cycles to provide a cardiac event count;

determining if the atria of the heart are in fibrillation responsive to said cardiac event count; and applying cardioverting electrical energy to the atria of the heart if the atria of the heart are in need of cardioversion.

59. A method as defined in claim 58 wherein said determining step includes determining if said cardiac event count is greater than a predetermined event count.

60. A method as defined in claim 58 including the further step of providing an average cardiac cycle event count for said plurality of cardiac cycles and wherein said determining step includes determining if said average cardiac cycle event count is greater than a predetermined average cardiac cycle event count.

61. A method as defined in claim 58 including the further step of establishing a heart activity sensing time, wherein said sensing step includes sensing said atrial electrical activity of the heart during said heart activity sensing time, wherein said method further includes the step of providing an average event count per unit of time for said plurality of cardiac cycles, and wherein said determining step includes determining if said average event count per unit of time is greater than a predetermined average event count per unit of time.

62. A method as defined in claim 58 including the further step of determining a total counting time for said plurality of cardiac cycles, wherein said method further includes the step of providing an average event count per unit of total counting time for said plurality of cardiac cycles, and wherein said determining step includes determining if said average event count per unit of total counting time is greater than a predetermined average event count per unit of counting time.

63. A method as defined in claim 58 wherein said establishing step includes establishing a single counting period for each said cardiac cycle.

64. A method as defined in claim 58 including the further steps of detecting R waves of the heart, and wherein said establishing step includes establishing each respective said time for counting with respect to a detected R wave.

65. A method as defined in claim 64 wherein said establishing step includes establishing a single counting period for each said cardiac cycle of said plurality of cardiac cycles.

66. A method as defined in claim 65 wherein said establishing step includes beginning each said counting period after the completion of each said detected R wave of each said cardiac cycle and terminating each said counting period before the T wave of each said cardiac cycle.

67. A method as defined in claim 66 wherein said establishing step includes beginning each said counting period about sixty milliseconds after the detected completion of each said detected R wave of each said cardiac cycle and terminating each said counting period about two hundred milliseconds after the detected completion of each said detected R wave of each said cardiac cycle.

68. A method as defined in claim 58 including the further steps of generating a time stamp for each one of said detected cardiac events, providing a memory, and storing said time stamps in said memory, and wherein said counting step includes counting only said time stamps stored in said memory occurring during each said time for counting.

* * * * *